United States Patent [19]

Nakajima et al.

[11] Patent Number: 5,002,958

[45] Date of Patent: Mar. 26, 1991

[54] HYPOTENSIVE AGENT

[75] Inventors: Yoshikage Nakajima, Tokyo; Mamoru Tanaka, Ohmiya; Tetsuya Tajima, Noda, all of Japan

[73] Assignee: Eisai Co., Ltd., Tokyo, Japan

[21] Appl. No.: 248,941

[22] Filed: Sep. 26, 1988

[30] Foreign Application Priority Data

Sep. 28, 1987 [JP] Japan ................... 62-243493

[51] Int. Cl.⁵ ................................. A61K 31/255
[52] U.S. Cl. ................................. 514/317
[58] Field of Search ......................... 514/317

[56] References Cited

U.S. PATENT DOCUMENTS 3,995,047 11/1976 Morita et al. ............ 546/237
4,075,335 2/1978 Wilhelm et al. .......... 514/274
4,701,462 10/1987 Wyllie ..................... 514/323

Primary Examiner—Allen J. Robinson
Attorney, Agent, or Firm—Birch, Stewart, Kolasch & Birch

[57] ABSTRACT

4'-ethyl-2-methyl-3-piperidinopropiophenone or a pharmacologically acceptable salt thereof is useful as a hypotensive agent.

5 Claims, 1 Drawing Sheet

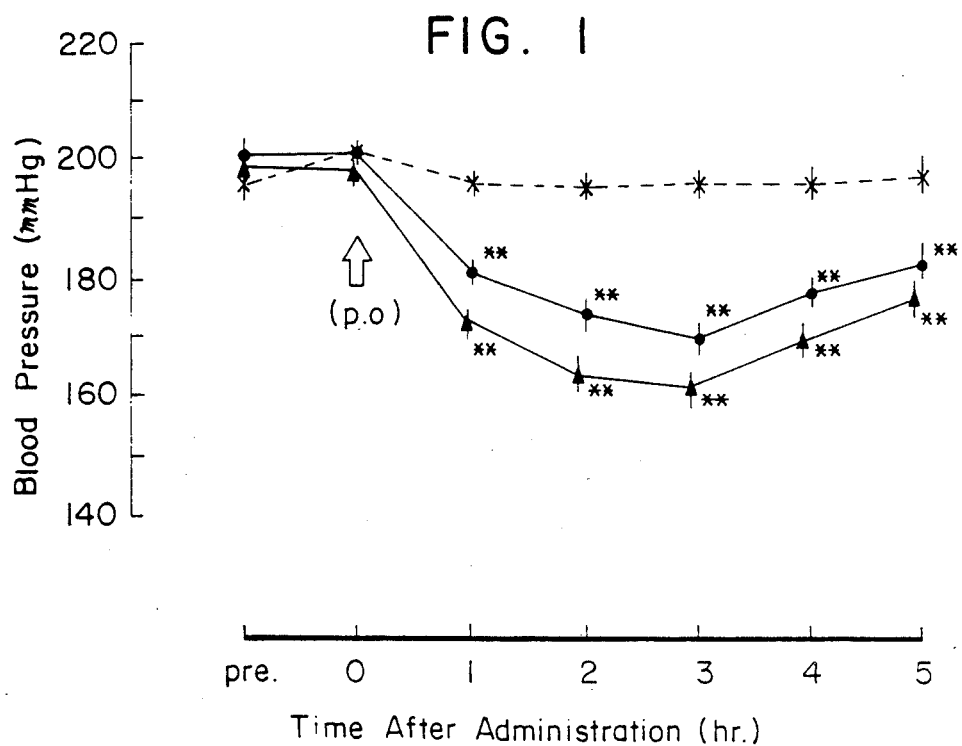
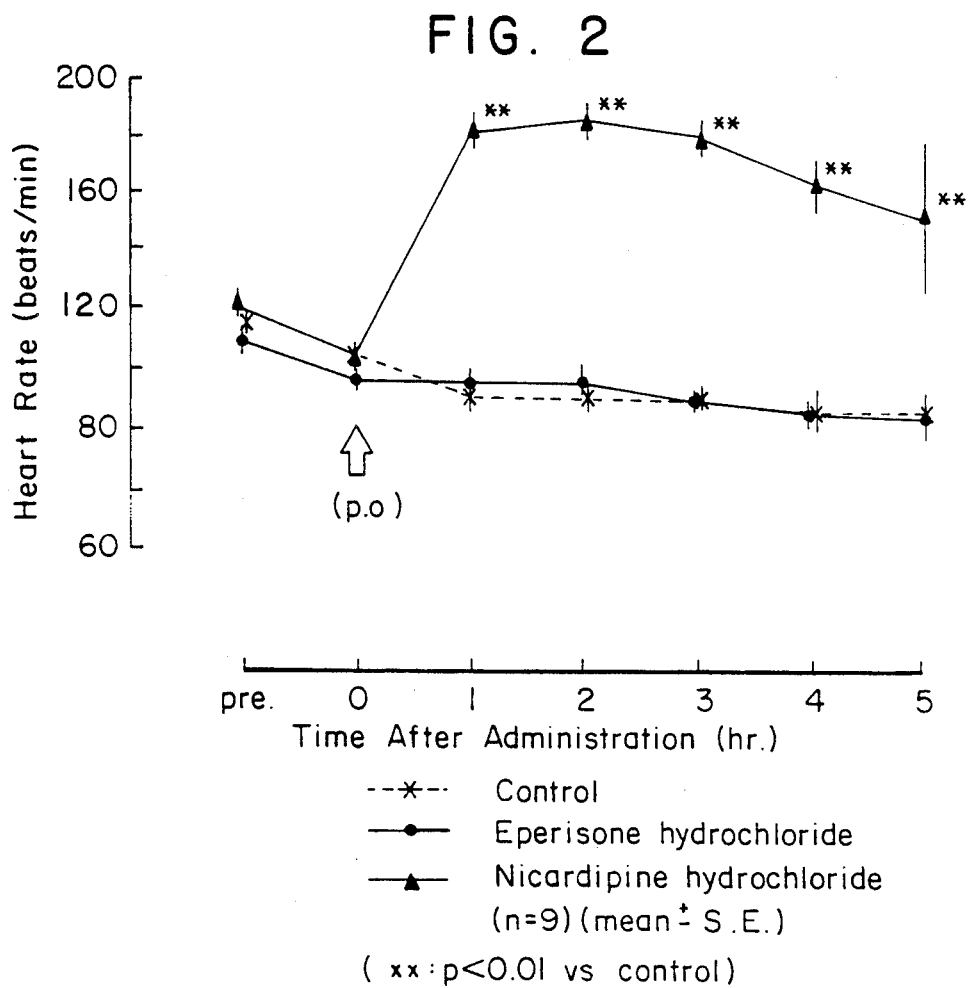

HYPOTENSIVE AGENT

The present invention relates to a hypotensive agent for the treatment or prevention of hypertension.

Statement of Prior Arts

Various hypotensive agents are used for the purpose of treating hypertension. However, they have various side effects and, therefore, they pose problems when they are administered in large amounts or during repeated administration over a long period. For example, diuretic hypotensive agents such as sulfonamide preparations and thiazide preparations have a serious side effect of inducing hyperuricemia and hypokalemia; sympatholytic agents such as reserpine preparations and methyldopa preparations have a side effect of inducing thirst, disturbance of consciousness and orthostatic hypotension; and vasodilators such as Apresoline have a side effect of inducing headache, tachycardia and angina. The development of safer hypotensive agents free of these defects is thus demanded.

Summary of the Invention

After intensive investigations made under these circumstances, the inventors have found that 4'-ethyl-2-methyl-3-piperidinopropiophenone of the following formula (I) and pharmacologically accetable salts thereof are useful as hypotensive agents. The present invention has been completed on the basis of this finding:

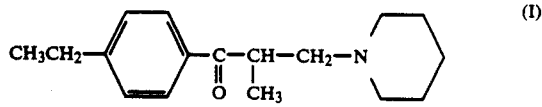

The invention relates to pharmaceutical use of 4'-ethyl-2-methyl-3-piperidinopropiophenone or a pharmacologically acceptable salt thereof.

The invention provides a method for treating or preventing the hypertension of a subject suffering from hypertension, which comprises administrating to a subject requiring such treatment a therapeutically effective amount of 4'-ethyl-2-methyl-3-piperidinopropiophenone or a pharmacologically acceptable salt thereof.

The invention provides a hypotensive agent comprising the above shown compound.

The invention provides use of 4'-ethyl-2-methyl-3-piperidinopropiophenone or a pharmacologically acceptable salt thereof for the preparation of pharmaceutical agent against hypertension.

The compound of the above structural formula has a nonpropietary name of eperisone. Its hydrochloride has been used heretofore for relieving muscle tonus in low back pains and cervical syndrome or for treating spastic paralysis induced by cerebral vascular lesions, etc.

After further intensive investigations of eperisone, the inventors have found also that surprisingly the compound (I) is effective as a hypotensive agent. It is surprising that this compound is effective for the treatment of hypertension, since the relieving of the muscle tonus is not related to the hypotensive effect from the viewpoint of the effects of medicines.

The pharmacologically acceptable salts herein include inorganic acid salts such as hydrochloride, hydrobromide and sulfate; organic acid salts such as acetate, maleate, tartrate, methanesulfonate, benzenesulfonate and toluenesulfonate; and amino acid salts such as argininate, aspartate and glutamate, among which the hydrochloride is the most desirable.

Eperisone hydrochloride of the following formula (II) which is a typical compound of the present invention can be prepared by, for example, the process described in Example 1 of Japanese Patent Publication No. 27914/1980.

The physico-chemical properties of this compound are as follows:

molecular formula: $C_{17}H_{25}NO \cdot HCl$
molecular weight: 295.85
structural formula:

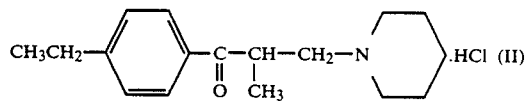

Physico-Chemical Properties

Eperisone hydrochloride is in the form of a white crystalline powder having a weak peculiar smell and a bitter taste. It is easily soluble in water, methanol, chloroform or glacial acetic acid, relatively easily soluble in ethanol, relatively difficultly soluble in acetic anhydride, difficultly soluble in acetone and scarcely soluble in ether.

This compound is optically inactive. Melting point: ca. 167° C. (dec.; after drying).

BRIEF DESCRIPTION OF THE DRAWING

FIG. 1 is a graph showing the effect of eperisone hydrochloride on the blood pressure of dogs suffering from Goldblatt hypertension.

FIG. 2 is a graph showing the effect of eperisone hydrochloride on the heart rate of dogs suffering from Goldblatt hypertension.

In the following animal tests, the hypotensive effect and toxicity of the compound of the present invention will be examined.

Pharmacological Experimental Example

1. Agents used

Epersions hydrochloride was a bitter, odorless, water-soluble compound in the form of white crystals having a molecular weight of 295.85. Nicardipine hydrochloride was used as a control. The dose was 5 ml/kg. Commercially available tablets were given as they were by oral administration.

2. Experimental animals

Female beagles suffering from Goldblatt hypertension of "one clip one kidney" type were used. They were prepared by removing the right kidney of each dog and narrowing the left renal artery to realize the hypertension.

3. Measurement of blood pressure and heart rate

The blood pressure and heart rate were measured in the artery of the tail of each dog in a closed manner with a device for continuously measuring the systolic pressure (SCS-301; a product of Shimadzu Seisakusho Ltd.).

Effects of Eperisone Hydrochloride Given Once by Oral Administration on the Blood Pressure and Heart Rate of Dogs Suffering from Goldblatt Hypertension The Goldblatt hypertension model was prepared as follows: the right kidney of each beagle was removed and the left renal artery was narrowed to realize the renal hypertension model of the "one clip one kidney" type. The effects of eperisone hydrochloride given once by oral administration on the blood pressure and heart beat were compared with those of nicardipine hydrochloride. The nine beagles were divided into three groups, i.e. a control group, a group to which 10 mg/kg of eperisone hydrochloride was given and another group to which 10 mg/kg of nicardipine hydrochloride was given. Nine beagles were subjected to the tests of all three groups. Namely, administration was discontinued at intervals of one week according to Latin square. The blood pressure and heart rate were measured before administration and then at specified intervals from one hour to five hours after administration.

The effects of eperisone hydrochloride on the blood pressure and heart rate of the beagles suffering from Goldblatt hypertension are shown in FIGS. 1 and 2.

In the control group, the initial blood pressure was $201\pm3$ mmHg, which was unchanged after 5 h. In the group of 10 mg/kg of eperisone hydrochloride, the blood pressure was $202\pm4$ mmHg before the administration and $172\pm3$ mmHg after 3 h. Thus, a significant reduction in the blood pressure was observed.

In the group of 10 mg/kg of nicardipine hydrochloride, it was $200\pm4$ mmHg before administration and $164\pm4$ mmHg after 3 h. Thus, a significant reduction in the blood pressure was also observed (see FIG. 1).

As for the heart rates shown in FIG. 2, no increase in the heart rate was observed with eperisone hydrochloride, while a significant increase ($p<0.01$) was observed as blood pressure was lowered with nicardipine hydrochloride. Namely, in the group of 10 mg/kg of nicardipine hydrochloride, the heart rate which was $106\pm7$ beats/min before the administration was increased to $184\pm15$ beats/min after 1 h and to a maximum of $189\pm6$ beats/min which was gradually recovered to $154\pm30$ beats/min. after 2 h, On the contrary, in the group of 10 mg/kg of eperisone hydrochloride, the heart rate before the administration was $97\pm5$ beats/min and that after one hour was $97\pm7$ beats/min. Substantially no increase in the heart rate was observed in the latter case.

Preparation of the Statistics

The analysis of variance was conducted by the time series analysis. The test groups were compared with the control group by Dunnet's method.

It is apparent from the results of the above pharmacological experiments that the compounds of the present invention have an excellent hypotensive effect.

Though the hypotensive effect of the compounds of the present invention was equivalent to that of nicardipine hydrochloride used in the comparison experiment, no tachycardia was induced at all by eperisone hydrochloride of the present invention, while the heart rate was considerably increased due to a sharp reduction in blood pressure when nicardipine hydrochloride was used.

The acute toxicity ($LD_{50}$) of eperisone hydrochloride is shown in Table 1.

TABLE 1

| | Acute toxicity $LD_{50}$ (mg/kg) | | | | | |
|---|---|---|---|---|---|---|
| | Mice (ICR) | | Rats (SD) | | Dogs (Beagles) | |
| Route | Male | Female | Male | Female | Male | Female |
| Oral | 1045 | 940 | 1300 | 1300 | >1078 | >750 |
| Intra-venous | 43.0 | 43.5 | 51.0 | 60.0 | — | — |

The compound of the present invention can be administered as the hypotensive agent parenterally in the form of injections, suppositories, external preparations or intravenous drip infusions or orally in the form of powders, granules, capsules or syrups.

The dose is not particularly limited, since it varies depending on the symptoms, age and manner of the administration (either oral or parenteral administration). Usually the dose for adults is about 10 to 800 mg, preferably about 50 to 500 mg and still preferably 50 to 200 mg a day. It is given in several portions a day.

In the formulation, a desired preparation is prepared by using any ordinary carrier by any ordinary method.

The compound of the present invention can be formulated into a preparation to be administered by any of conventional formulation methods. Therefore, the present invention includes also a preparation composition comprising at least one compound of the invention and suitable for use as a medicine for human beings. The composition containing any necessary pharmaceutical carrier or excipient is used by any ordinary method.

The composition is provided preferably in a form suitable for absorption through the digestive tract.

In the preparation of the injections, additives such as a pH adjustor, buffering agent, suspending agent, solubilizer, stabilizer, isotonizer and preservative are added, if necessary, to the active ingredient and the injections such as subcutaneous, intramuscular or intravenous injections are prepared by an ordinary method.

The suspending agents include, for example, methylcellulose, Polysorbate 80, hydroxyethylcellulose, acacia, powdery tragacanth, sodium carboxymethyl-cellulose and polyoxyethylene sorbitan monolaurate. The solubilizers include, for example, propylene glycol, polyoxyethylene-hardened castor oil, Polysorbate 80, nicotinamide, polyoxyethylene sorbitan monolaurate, macrogol, ethyl ester of castor oil fatty acid, and glucose. The stabilizers include, for example, sodium sulfite, sodium metasulfate and ether. The preservatives include, for example, methyl p-hydroxybenzoate, ethyl p-hydroxybenzoate, sorbic acid, phenol, cresol and chlorocresol.

An oral solid preparation is prepared by adding an excipient and, if necessary, a binder, disintegrator, lubricant, colorant, corrigent, etc. to the active ingredient and shaping the mixture into tablets, coated tablets, granules, powders or capsules by any ordinary method.

The excipients include, for example, lactose, corn starch, white sugar, glucose, sorbitol, crystalline cellulose and silicon dioxide. The binders include, for example, polyvinyl alcohol, polyvinyl ether, ethylcellulose, methylcellulose, acacia, tragacanth, gelatin, shellac, hydroxy-propylcellulose, hydroxypropylstarch and polyvinyl-pyrrolidone. The disintegrators include, for example, starch, agar, gelatin powder, crystalline cellulose, calcium carbonate, sodium hydrogencarbonate, calcium citrate, dextrin and pectin. The lubricants include, for example, magnesium stearate, talc, polyethylene glycol, silica and hardened vegetable oils. The colorants include those accepted as colorants for medicines. The corrigents include, for example, cocoa powder, menthol, aromatic powder, peppermint oil, borneol and cinnamon powder. These tablets and granules can be suitably coated with sugar, gelatin, etc.

We claim:

1. A method for treating the hypertension of a subject suffering from hypertension, which comprises administrating to a subject requiring such treatment an antihypertensive effective amount of 4'-ethyl-2-methyl-3-piperidinopropiophenone or a pharmacologically acceptable salt thereof.

2. The method according to claim 1, wherein said antihypertensive effective amount is 10 mg/kg body weight.

3. The method according to claim 1, wherein said antihypertensive amount is administered as a dose of from about 10 to 800 mg/day.

4. The method according to claim 3, wherein said dose is 50 to 500 mg/day.

5. The method according to claim 4, wherein said dose is 50 to 200 mg/day.